(12) United States Patent
Kiminami et al.

(10) Patent No.: US 9,642,934 B2
(45) Date of Patent: May 9, 2017

(54) BONE REGENERATION MATERIAL KIT, PASTE-LIKE BONE REGENERATION MATERIAL, BONE REGENERATION MATERIAL, AND BONE BONDING MATERIAL

(71) Applicants: GUNZE LIMITED, Ayabe-shi, Kyoto (JP); Meiji University, Tokyo (JP); Kanagawa Academy of Science and Technology, Kawasaki-shi, Kanagawa (JP)

(72) Inventors: Keishi Kiminami, Kyoto (JP); Hidetoshi Arimura, Kyoto (JP); Mamoru Aizawa, Kanagawa (JP); Minori Mizumoto, Kanagawa (JP); Toshiisa Konishi, Kanagawa (JP)

(73) Assignees: Gunze Limited, Kyoto (JP); Meiji University, Tokyo (JP); Kanagawa Academy of Science and Technology, Kanagawa (JP)

(*) Notice: Subject to any disclaimer, the term of this patent is extended or adjusted under 35 U.S.C. 154(b) by 0 days.

(21) Appl. No.: 14/910,183

(22) PCT Filed: Aug. 8, 2014

(86) PCT No.: PCT/JP2014/071007
§ 371 (c)(1),
(2) Date: Feb. 4, 2016

(87) PCT Pub. No.: WO2015/020192
PCT Pub. Date: Feb. 12, 2015

(65) Prior Publication Data
US 2016/0175481 A1 Jun. 23, 2016

(30) Foreign Application Priority Data
Aug. 9, 2013 (JP) ................................ 2013-167002

(51) Int. Cl.
| | | |
|---|---|---|
| A61L 27/54 | (2006.01) | |
| A61L 27/58 | (2006.01) | |
| A61L 27/12 | (2006.01) | |
| A61L 27/22 | (2006.01) | |

(52) U.S. Cl.
CPC .......... *A61L 27/12* (2013.01); *A61L 27/222* (2013.01); *A61L 27/54* (2013.01); *A61L 27/58* (2013.01); *A61L 2300/112* (2013.01); *A61L 2300/412* (2013.01); *A61L 2430/02* (2013.01)

(58) Field of Classification Search
CPC ......... A61L 2300/112; A61L 2300/412; A61L 2430/02; A61L 27/12; A61L 27/222; A61L 27/54; A61L 27/58
See application file for complete search history.

(56) References Cited

U.S. PATENT DOCUMENTS 8,101,676 B2 * 1/2012 McKay ............... A61K 38/1875
424/423
2010/0132593 A1 6/2010 Aizawa et al.

FOREIGN PATENT DOCUMENTS

| JP | 2000-245823 | 9/2000 |
|---|---|---|
| JP | 2000-262609 | 9/2000 |
| JP | 2002-035106 | 2/2002 |
| JP | 2008-200476 | 9/2008 |
| JP | 2009-183498 | 8/2009 |
| JP | 2011-015957 | 1/2011 |
| JP | 2012-228383 | 11/2012 |
| WO | 2008/090648 | 7/2008 |

OTHER PUBLICATIONS

Konishi, et al., "Novel chelate-setting calcium phosphate cements fabricated with wet-synthesized hydroxyapatite powder", Journal of Materials Science. Materials in Medicine, vol. 24, No. 3, 2013 (published online: Dec. 2012), pp. 611-621.
Konishi, et al., "Fabrication of chelate-setting cements from hydroxyapatite powders surface-modified with various sodium inositol hexaphosphate concentrations and their mechanical properties", Procedia Engineering, vol. 36, 2012, pp. 137-143.

* cited by examiner

*Primary Examiner* — Ernst V Arnold
(74) *Attorney, Agent, or Firm* — Hamre, Schumann, Mueller & Larson, P.C.

(57) ABSTRACT

The present invention aims to provide a bone regeneration material kit, a paste-like bone regeneration material, a bone regeneration material, and a bone bonding material, which contain particles including a bioabsorbable polymer; and can fill a bone defect or damage and secure the mechanical strength of the bone in the short term and can promote regeneration of the patient's own bone in the long term. In addition, they can exhibit anti-washout properties after filling even when they are in contact with water such as blood or biological fluids. The present invention relates to a bone regeneration material kit comprising: a particle comprising a calcium salt and having an inositol phosphate or salt thereof adsorbed on the surface; a particle comprising a bioabsorbable polymer; and an aqueous medium.

7 Claims, No Drawings

BONE REGENERATION MATERIAL KIT, PASTE-LIKE BONE REGENERATION MATERIAL, BONE REGENERATION MATERIAL, AND BONE BONDING MATERIAL

TECHNICAL FIELD

The present invention relates to a bone regeneration material kit, a paste-like bone regeneration material, a bone regeneration material, and a bone bonding material, which contain particles comprising a bioabsorbable polymer; and can fill a bone defect or damage and secure the mechanical strength of the bone in the short term and can promote regeneration of the patient's own bone in the long term. In addition, they can exhibit anti-washout properties after filling even when they are in contact with water such as blood or biological fluids.

BACKGROUND ART

A bone defect or damage has been treated with artificial bone.

Dense and porous calcium phosphate artificial bone has been conventionally known. Such artificial bone needs to be processed in shape to fit the state of bone to be treated. However, such artificial bone is hard to cut or shave in an operation site, and is therefore difficult to use.

For such problems, paste-like bone filling materials which are suspensions of calcium phosphate granules in an aqueous medium have been suggested (for example, Patent Literature documents 1 to 3). Such paste-like bone filling materials can be used to fill a bone defect or damage using an injector or the like. The paste-like bone filling materials cure after filling and fixed at the bone defect or damage. The use of the paste-like bone filling materials enables easy treatment of even a complicated bone defect or damage.

However, the paste-like bone filling materials described in Patent Literature documents 1 to 3 can only fill a bone defect or damage, but cannot promote bone regeneration. Actually, bone regeneration occurs only at the surface of a bone filling material used for filling. The bone filling materials have very high mechanical strength, but are poor in elasticity and toughness because they do not contain an organic component of bone tissues, such as collagen fibers. This is a fatal disadvantage of the material. For this reason, bone regeneration materials have been required to fill a bone defect or damage and secure the mechanical strength of the bone in the short term and promote regeneration of the patient's own bone in the long term.

For such problems, Patent Literature 4 discloses a bone regeneration material kit including particles comprising a calcium phosphate compound, particles comprising a bioabsorbable polymer, and an aqueous medium. When the bone regeneration material kit described in Patent Literature 4 is used to fill a bone defect or damage, bioabsorption of the particles comprising a bioabsorbable polymer occurs, and continuous pores generate in a filled portion. Osteoblastic cells enter the continuous pores and grow therein. That is, the bone regeneration material kit described in Patent Literature 4 can fill a bone defect, and further serve as a scaffold material for growth of osteoblastic cells.

CITATION LIST

Patent Literature

Patent Literature 1: JP 2000-262609 A
Patent Literature 2: JP 2000-245823 A
Patent Literature 3: JP 2002-35106 A
Patent Literature 4: JP 2011-15957 A

SUMMARY OF INVENTION

Technical Problem

In practice, a bone regeneration material kit is used in the following way: particles comprising a calcium phosphate compound, particles comprising a bioabsorbable polymer, and an aqueous medium, which are included in the kit, are mixed to prepare a paste-like bone regeneration material in an operation site, the resulting paste-like bone regeneration material is used to fill a bone defect or damage using an injector or the like, and wound closure is performed to complete the surgery. However, much water such as blood or biological fluids is usually present at an area to be filled with the paste-like bone regeneration material. The paste-like bone regeneration material once attached at the area absorbs water and disintegrates. As a result, the material cannot fill a bone defect.

In view of the above current state of the art, the present invention aims to provide a bone regeneration material kit, a paste-like bone regeneration material, a bone regeneration material, and a bone bonding material, which contain particles comprising a bioabsorbable polymer; and can fill a bone defect or damage and secure the mechanical strength of the bone in the short term and can promote regeneration of the patient's own bone in the long term. In addition, they can exhibit anti-washout properties after filling even when they are in contact with water such as blood or biological fluids.

Solution to Problem

One aspect of the present invention relates to a bone regeneration material kit comprising:
a particle comprising a calcium salt and having an inositol phosphate or salt thereof adsorbed on the surface;
a particle comprising a bioabsorbable polymer; and
an aqueous medium.

The present invention is described in detail below.

The present inventors made intensive investigations and consequently have found that combination use of a particle comprising a bioabsorbable polymer and a particle comprising a calcium salt and having an inositol phosphate or salt thereof adsorbed on the surface, provides a material which exhibits an anti-washout property after filling even when it is in contact with water such as blood or biological fluids. Thereby, the present invention has been completed. The reason for the anti-washout property is not clear, but is thought to be due to interaction between a particle comprising a bioabsorbable polymer and an inositol phosphate or salt thereof adsorbed on the surface of a particle comprising a calcium salt.

The bone regeneration material kit of the present invention includes a particle comprising a calcium salt and having an inositol phosphate or salt thereof adsorbed on the surface (hereinafter, also referred to as "an inositol phosphate-adsorbing calcium salt particle); a particle comprising a bioabsorbable polymer; and an aqueous medium.

A mixture of the particle comprising a calcium salt and having an inositol phosphate or salt thereof adsorbed on the surface and an aqueous medium is in the form of a paste. Such a mixture cures in the body and enhances the mechanical strength of bone. Further, due to the interaction between the inositol phosphate or salt thereof adsorbed on the surface of the calcium salt particle and the particle comprising a bioabsorbable polymer, a paste-like bone regeneration material obtained can exhibit a sufficient anti-washout property only by relatively short-time curing.

The inositol phosphate-adsorbing calcium salt particles can be prepared by, for example, immersing and grinding the calcium salt particles in an aqueous solution of the inositol phosphate or salt thereof. The inositol phosphate or salt thereof is considered to be chemically adsorbed on the surfaces of the calcium salt particles.

Examples of the calcium salt include calcium phosphate and calcium carbonate. Each of these calcium salts may be used alone, or two or more of these may be used in combination. In particular, calcium phosphate is preferred.

Examples of the calcium phosphate include hydroxyapatite, α-tricalcium phosphate, β-tricalcium phosphate, tetracalcium phosphate, octacalcium phosphate, calcium hydrogen phosphate, calcium dihydrogen phosphate, and amorphous calcium phosphate. Each of these calcium phosphates may be used alone, or two or more of these may be used in combination. In particular, hydroxyapatite, α-tricalcium phosphate, and β-tricalcium phosphate are preferred. Hydroxyapatite is more preferred.

The lower limit of the specific surface area of the calcium salt particles is preferably 0.1 $m^2/g$. The upper limit of the specific surface area thereof is preferably 120 $m^2/g$. A sufficient amount of the inositol phosphate or salt thereof can be adsorbed on the surfaces of the calcium salt particles having a specific surface area within the above range. The lower limit of the specific surface area is more preferably 20 $m^2/g$, still more preferably 40 $m^2/g$.

The specific surface area of the calcium salt particles can be determined by the BET method using a Micromeritics automated specific surface area measuring apparatus FlowSorb III 2305 (produced by Shimadzu Corporation).

Examples of the inositol phosphate include inositol monophosphate, inositolbisphosphate, inositol trisphosphate, inositol tetrakisphosphate, inositol pentaphosphate, and phytic acid (inositol hexaphosphate).

The salt of inositol phosphate may be an alkali metal salt or alkaline-earth metal salt. Specific examples thereof include sodium salt, potassium salt, magnesium salt, calcium salt, and barium salt. Each of these inositol phosphates or salts thereof may be used alone, or two or more of these may be used in combination. In particular, phytic acid, sodium phytate, and potassium phytate are preferred.

Several kinds of sodium phytates different in crystal water content are known. Examples thereof include sodium phytate octatriacontahydrate, sodium phytate heptatetracontahydrate, and sodium phytate dodecahydrate. All of these can be preferably used.

The concentration of the inositol phosphate or salt thereof in the aqueous solution is not particularly limited. It is preferably 1000 to 11000 ppm, more preferably 5000 to 11000 ppm, still more preferably 7000 to 10000 ppm.

It is preferred that, when the aqueous solution of the inositol phosphate or salt thereof is prepared, an alkaline aqueous solution is added to the solution before it is used to control the pH of the solution within the range of preferably 6 to 11, more preferably 6 to 8. Examples of the alkaline aqueous solution for pH control include, but are not limited to, an aqueous solution of sodium hydroxide and an aqueous solution of potassium hydroxide.

The calcium salt particles may be immersed and ground in the aqueous solution of the inositol phosphate or salt thereof by any method. For example, the calcium salt particles are added to the aqueous solution of the inositol phosphate or salt thereof which is kept warm at preferably 20° C. to 60° C., more preferably 20° C. to 40° C., and they are stirred or shaken for preferably 0.5 to 24 hours, more preferably 0.5 to 10 hours using a disintegrator.

In this case, the molar ratio of the inositol phosphate or salt thereof to the calcium salt is preferably 0.001 to 0.1, more preferably 0.01 to 0.08.

Thus, the inositol phosphate or salt thereof is adsorbed on the surfaces of the particles comprising a calcium salt by mixing the particles comprising a calcium salt with the aqueous solution of the inositol phosphate or salt thereof. Then, the resulting particles are separated and dried to give the inositol phosphate-adsorbing calcium salt particles.

The lower limit of the average particle size of the inositol phosphate-adsorbing calcium salt particles is preferably 0.5 μm. The upper limit of the average particle size thereof is preferably 100 μm. If the average particle size of the inositol phosphate-adsorbing calcium salt particles is smaller than 0.5 μm, a paste prepared by mixing the particles and the aqueous medium is highly viscous, and may therefore be hardly injected. If the average particle size thereof is larger than 100 μm, the cured product has low strength, and may therefore not sufficiently enhance the mechanical strength of bone. The upper limit of the average particle size of the inositol phosphate-adsorbing calcium salt particles is more preferably 50 μm.

The bone regeneration material kit of the present invention preferably further includes a particle comprising a calcium phosphate compound and having no inositol phosphate or no salt thereof on the surface (hereinafter, also simply referred to as "a particle comprising a calcium phosphate compound). The use of the particle comprising a calcium phosphate compound in combination with the inositol phosphate-adsorbing calcium salt particle enables improvement in the mechanical strength of the cured product.

The mechanical strength of the cured product can be changed by controlling the time for preparing the particles comprising a calcium phosphate compound by grinding.

Examples of the calcium phosphate compound include, but are not limited to, α-tricalcium phosphate, β-tricalcium phosphate, tetracalcium phosphate, octacalcium phosphate, calcium hydrogen phosphate, calcium dihydrogen phosphate, amorphous calcium phosphate, hydroxyapatite, carbon-containing apatite, fluorine apatite, bone mineral-containing apatite, and silicon-containing apatite. Each of these calcium phosphate compounds may be used alone, or two or more of these may be used in combination. In particular, α-tricalcium phosphate and β-tricalcium phosphate are preferred, and α-tricalcium phosphate is more preferred.

The lower limit of the average particle size of the particles comprising a calcium phosphate compound is preferably 0.5 μm. The upper limit of the average particle size thereof is preferably 100 μm. If the average particle size of the particles comprising a calcium phosphate compound is smaller than 0.5 μm, a paste prepared by mixing the particles with the aqueous medium is highly viscous, and may therefore be hardly injected. If the average particle size thereof is larger than 100 μm, the cured product has low strength, and may not sufficiently enhance the mechanical strength of bone. The upper limit of the average particle size of the particles comprising a calcium phosphate compound is more preferably 50 μm.

The particles comprising a bioabsorbable polymer are gradually absorbed into the body after operation, whereby continuous pores osteoblastic cells can enter are formed in the filled portion.

Examples of the bioabsorbable polymer include natural polymers such as proteins (e.g. gelatin, collagen, hyaluronic acid, albumin, fibrin) and polysaccharides (e.g. starch, alginic acid, chitin, pectic acid, and derivatives thereof); and synthetic polymers such as polylactic acid, polyglycolic acid, a lactic acid/glycolic acid copolymer, a glycolic acid/ε-caprolactone copolymer, a lactic acid/ε-caprolactone copolymer, polymalic acid, poly-α-cyanoacrylate, poly-β-hydroxy acid, polytrimethylene oxalate, polytetramethylene oxalate, polyortho ester, polyortho carbonate, polyethylene carbonate, poly-γ-benzyl-L-glutamate, poly-L-glutamic acid, poly-γ-methyl-L-glutamate, poly-L-lysine, and poly-L-alanine. Each of these bioabsorbable polymers may be used alone, or two or more of these may be used in combination.

When the particles comprising a bioabsorbable polymer are made from gelatin, collagen, or hyaluronic acid, the gelatin, collagen, or hyaluronic acid is preferably crosslinked.

In particular, crosslinked gelatin is preferred. In cases where a particle comprising crosslinked gelatin is used as the particle comprising a bioabsorbable polymer, a resulting material cured in a remarkably short time can exhibit a sufficient anti-washout property. Crosslinked gelatin is a highly hydrophilic polymer, which absorbs water and swells. Therefore, when a material that contains particles comprising crosslinked gelatin is implanted into a bone defect, the material absorbs the surrounding water and increases in volume, and is adhered well in a filled portion. If a conventional paste-like bone filling material containing only an inorganic material is used at an area with a large amount of biological fluids or blood, delay of curing or leakage of uncured materials may occur. Further, even if the material cures, reduction in strength or leakage of disintegrated materials may occur. On the other hand, the use of particles comprising highly hydrophilic crosslinked gelatin provides the hemostatic effect. Therefore, such particles can be used even at an area with some bleeding.

The state of the cross-linkage of the particles comprising crosslinked gelatin can be controlled by adjustment of the conditions for crosslinking gelatin by a conventionally known crosslinking method such as thermal dehydration crosslinking, ultraviolet light crosslinking, chemical crosslinking, or ion crosslinking. For example, thermal crosslinking of particles comprising uncrosslinked gelatin is performed by heating at a temperature within the range of 110° C. to 170° C. for five minutes to 48 hours under vacuum. The state of the cross-linkage of the particles comprising crosslinked gelatin can be controlled by adjusting the crosslinking temperature or heating time.

The particles comprising a bioabsorbable polymer may be treated with radiation before use, such as γ-rays or electron beam. The use of radiation-treated particles comprising a bioabsorbable polymer enables maintaining the excellent performance of the bone regeneration material kit and improvement in the mechanical strength of the cured product. An additional advantage is that since the particles comprising a bioabsorbable polymer are sterilized by the radiation treatment, there is no need to perform additional sterilization of the particles, such as sterilization by ethylene oxide gas.

The lower limit of the average particle size of the particles comprising a bioabsorbable polymer is preferably 10 μm. The upper limit of the average particle size thereof is preferably 400 μm. If the average particle size of the particles comprising a bioabsorbable polymer is smaller than 10 μm, continuous pores for osteoblastic cell entry may not be formed. If the particle size thereof is larger than 400 μm, the resulting cured product has low strength, which may not sufficiently enhance the mechanical strength of bone. The lower limit of the average particle size of the particles comprising a bioabsorbable polymer is more preferably 20 μm. The upper limit of the average particle size thereof is more preferably 200 μm.

The aqueous medium is used as a medium for the paste-like bone regeneration material.

Examples of the aqueous medium include injectable water. The aqueous medium may contain a buffer component to adjust the pH. The aqueous medium may be bone marrow or a cell suspension.

Further, the aqueous medium may contain, for example, a small amount of water-soluble polymer to adjust the viscosity, an antimicrobial agent to prevent infection, or any type of growth factor to promote bone regeneration.

Examples of the water-soluble polymer include polymers of lactic acid, glycolic acid, succinic acid, maleic acid, fumaric acid, and malic acid; chondroitin sulfuric acid; hyaluronic acid; dextran sulfuric acid; heparan sulfuric acid; alginic acid; and chitosan.

The bone regeneration material kit of the present invention may further contain any type of drug such as a cell growth factor, an antimicrobial agent, or an antibiotic. The bone regeneration material kit containing such a drug(s) used to fill a bone defect or damage decomposes after curing and gradually releases the drug(s). Therefore, the effects of the drug(s) can last for a long period of time. For example, rapid bone regeneration is expected to be achieved by sustained-release of a cell growth factor. Furthermore, due to sustained-release of an antimicrobial agent, antibiotic, or the like, the kit can be used even for bone defects at or around which many bacterium are present (for example, in the case of infected bone or in an oral cavity). Further, a good curative effect is expected to be achieved by combination use of a cell growth factor and bone marrow cells containing bone marrow mesenchymal cells, for example, in the case of non-union fractures or vertebral compression fracture associated with osteoporosis, in which cells needed for bone formation are presumably not enough at or around bone to be repaired, or in the case where cells effective for bone formation may not reach the center of bone to be repaired. The drug is not limited to bone regeneration-related drugs.

A paste-like bone regeneration material can be prepared using the bone regeneration material kit of the present invention.

The paste-like bone regeneration material herein means a bone regeneration material which is in paste form during use, can be readily used to fill a bone defect or damage manually or with an injector, and can cure in the body after filling.

Another aspect of the present invention relates to a paste-like bone regeneration material, which is a paste prepared by mixing the particle comprising a calcium salt and having an inositol phosphate or salt thereof adsorbed on the surface; the particle comprising a bioabsorbable polymer; and the aqueous medium of the bone regeneration material kit of the present invention.

In the preparation of the paste-like bone regeneration material of the present invention, the inositol phosphate-adsorbing calcium salt particles, the particles comprising a bioabsorbable polymer, and the aqueous medium may be blended at any ratio. The ratio is determined in consideration of easiness of mixing operation, easiness of injection using an injector, the setting time, or the strength of the cured product.

The porosity of the cured product can be controlled by adjusting the blend ratio of the inositol phosphate-adsorbing calcium salt particles and the particles comprising a bioabsorbable polymer. Thereby, the strength of the cured product and the bone regeneration speed can be controlled.

The blend ratio of the inositol phosphate-adsorbing calcium salt particles (in the case of containing the calcium phosphate compound, the total of the inositol phosphate-adsorbing calcium salt particles and the calcium phosphate compound) and the particles comprising a bioabsorbable polymer is preferably within the range of 97:3 to 76:24 by weight. When the ratio is within the above range, the mechanical strength of bone can be secured in the short term and bone can be regenerated in the long term. If the proportion of the particles comprising a bioabsorbable polymer is less than that in the above range, continuous pores are not sufficiently formed, which may result in poor regeneration of bone. If the proportion of the particles comprising a bioabsorbable polymer is more than that in the above range, the strength of the cured product may be low. The ratio is more preferably within the range of 95:5 to 80:20 by weight, still more preferably within the range of 90:10 to 85:15 by weight.

The strength needed for the bone regeneration material differs according to an area at which the material is used. Therefore, the blend ratio may be determined in consideration of an area at which the material is used, within the range of the preferred blend ratio of the inositol phosphate-adsorbing calcium salt particles and the particles comprising a bioabsorbable polymer.

For example, the strength needs to be prioritized rather than the bone regeneration speed in the material when the material is used at an area to which a great load is applied, such as calcaneus, femur, tibia, or vertebra. That is, the proportion of the particles comprising a bioabsorbable polymer is set relatively low.

For example, the bone regeneration speed needs to be prioritized rather than the strength in the material when the material is used at an area to which no great load is applied, such as skull, humerus, forearm bone (radio-ulna), or phalange. That is, the proportion of the particles comprising a bioabsorbable polymer is set relatively high.

In cases where the bone regeneration material kit of the present invention contains the calcium phosphate compound, the blend ratio of the inositol phosphate-adsorbing calcium salt particles and the calcium phosphate compound is preferably within the range of 90:10 to 10:90 by weight in the preparation of the paste-like bone regeneration material. Within such a range, the mechanical strength of the cured product can be improved. The blend ratio is more preferably within the range of 10:90 to 50:50 by weight.

The lower limit of the amount of the aqueous medium is preferably 50 parts by weight and the upper limit of the amount thereof is preferably 150 parts by weight, relative to 100 parts by weight of the total of the inositol phosphate-adsorbing calcium salt particles and the particles comprising a bioabsorbable polymer. A paste-like bone regeneration material containing the aqueous medium in an amount of less than 50 parts by weight is highly viscous, and may be difficult to be injected. A paste-like bone regeneration material containing the aqueous medium in an amount of more than 150 parts by weight may shrink during curing. The lower limit of the amount of the aqueous medium is more preferably 60 parts by weight. The upper limit of the amount thereof is more preferably 100 parts by weight.

The inositol phosphate-adsorbing calcium salt particles, the particles comprising a bioabsorbable polymer, and the aqueous medium may be mixed by any method. It is preferred that the inositol phosphate-adsorbing calcium salt particles, the particles comprising a bioabsorbable polymer, and the aqueous medium are put into a syringe and mixed and kneaded therein, or the inositol phosphate-adsorbing calcium salt particles, the particles comprising a bioabsorbable polymer, and the aqueous medium are manually mixed and kneaded in advance.

When the paste-like bone regeneration material of the present invention is prepared, the inositol phosphate-adsorbing calcium salt particles, the particles comprising a bioabsorbable polymer, and the aqueous medium may be blended in any order. The total amount of the inositol phosphate-adsorbing calcium salt particles, the particles comprising a bioabsorbable polymer, and the aqueous medium may be simultaneously mixed.

Preferred is a method in which the inositol phosphate-adsorbing calcium salt particles and the particles comprising a bioabsorbable polymer are mixed, and then the aqueous medium is added to the mixture; or a method in which part of the aqueous medium is added to the inositol phosphate-adsorbing calcium salt particles and they are mixed and kneaded, and then the particles comprising a bioabsorbable polymer and the rest of the aqueous medium are added thereto and they are mixed. The paste-like bone regeneration material prepared in such a manner can provide a bone regeneration material with high strength.

The paste-like bone regeneration material of the present invention can be readily used to fill a bone defect or damage manually or with an injector such as a syringe. The paste-like bone regeneration material after filling cures even at room temperature to turn into a bone regeneration material which enhances the mechanical strength of bone. The paste-like bone regeneration material of the present invention which includes the inositol phosphate-adsorbing calcium salt particles as well as the particles comprising a bioabsorbable polymer in combination exhibits an anti-washout property after filling even when it is in contact with water such as blood or biological fluids. After operation, the particles comprising a bioabsorbable polymer are absorbed with time and continuous pores are formed. Osteoblastic cells enter the continuous pores, leading to regeneration of the patient's own bone.

A bone regeneration material prepared outside the body by curing the paste-like bone regeneration material of the present invention may be used to fill a bone defect or damage, or may be used as a bone bonding material. Another aspect of the present invention relates to a bone regeneration material or a bone bonding material prepared by curing the paste-like bone regeneration material of the present invention.

Advantageous Effects of Invention

The present invention can provide a bone regeneration material kit, a paste-like bone regeneration material, a bone regeneration material, and a bone bonding material, which contain particles comprising a bioabsorbable polymer; and can fill a bone defect or damage and secure the mechanical strength of the bone in the short term and can promote regeneration of the patient's own bone in the long term. In addition, they can exhibit anti-washout properties after filling even when they are in contact with water such as blood or biological fluids.

DESCRIPTION OF EMBODIMENTS

The following describes examples to more specifically illustrate embodiments of the present invention. It should be noted that the present invention is not limited only to these examples.

Experimental Example 1

(1) Preparation of Wet-Synthesized Hydroxyapatite Powder

First, 1000 mL of a 0.5 M suspension of calcium hydroxide was prepared. To the suspension was added dropwise 1000 mL of a 0.3M aqueous solution of phosphoric acid. The concentrations of calcium hydroxide and phosphoric acid were adjusted so that they satisfy Ca/P=1.67 (molar ratio). The pH in a reaction chamber was adjusted with a pH adjuster (25% ammonia water) to meet 10<pH<11. After completion of the dropping of the aqueous solution of phosphoric acid, the mixture was further stirred for one hour and then allowed to stand in an incubator set at 37° C. for 24 hours for maturation. After maturation, the slurry was recovered by suction filtration and frozen overnight in a freezer at −80° C. The frozen slurry was dried for 48 hours using a freeze dryer (Free Zone (trademark), produced by Labconco) to give a wet-synthesized hydroxyapatite powder.

(2) Preparation of Inositol Hexaphosphate-Adsorbing Hydroxyapatite Particles

A 8.00 g portion of a 50% by weight aqueous solution of inositol hexaphosphate (produced by Wako Pure Chemical Industries) was accurately weighed, diluted to about 300 mL with purified water, then adjusted to pH 7.3 with an aqueous solution of sodium hydroxide and hydrochloric acid, and diluted to 500 mL in a measuring cylinder. Thus, a 8000 ppm aqueous solution of inositol hexaphosphate was prepared.

The inositol hexaphosphate was adsorbed on the hydroxyapatite using a planetary ball mill (type P-6, produced by FRITCH) under the following conditions. To a zirconia pot were added 50 mL of the resulting aqueous solution of inositol hexaphosphate, 10.0 g of the wet-synthesized hydroxyapatite powder (average particle size 10 μm), and 180 g of Φ2 mm zirconia balls. They were stirred at a rotation speed of 300 rpm for one hour, followed by centrifugation at 9000 rpm for 30 minutes. The resulting residue was filtered to obtain a slurry. The slurry was frozen overnight at −80° C. The frozen slurry was freeze dried for 24 hours using a freeze dryer (Free Zone (trademark), produced by LABCONCO) to give inositol hexaphosphate-adsorbing hydroxyapatite particles.

(3) Preparation of Ground Product of α-Tricalcium Phosphate Particles

α-tricalcium phosphate was ground using a planetary ball mill (type P-6, produced by FRITCH) under the following conditions. To a zirconia pot were added 40 mL of purified water, 10.0 g of α-tricalcium phosphate particles (average particle size 10 μm, produced by TAIHEI CHEMICAL INDUSTRIAL CO., LTD.), and 180 g of Φ2 mm zirconia balls. They were stirred at a centrifugal acceleration of 300 rpm for one hour, followed by filtration. The resulting product was frozen overnight at −80° C. The frozen slurry was freeze dried for 24 hours using a freeze dryer (Free Zone (trademark), produced by LABCONCO) to give a ground product of α-tricalcium phosphate particles.

(4) Preparation of Powder Mixture of Inositol Hexaphosphate-Adsorbing Hydroxyapatite Particles and Ground Product of α-Tricalcium Phosphate Particles A V-type mixer (produced by TSUTSUI SCIENTIFIC INSTRUMENTS CO., LTD.) was charged with the inositol hexaphosphate-adsorbing hydroxyapatite particles and the ground product of α-tricalcium phosphate particles at a ratio of 0:100, 10:90, 20:80, 50:50, 80:20, or 100:0 by weight. They were stirred for 5 minutes to prepare a powder mixture.

(5) Production of Crosslinked Gelatin Particles

Uncrosslinked gelatin particles having an average particle size of 200 μm were heat-treated under vacuum at 140° C. for 14 hours to prepare thermally crosslinked gelatin particles.

(6) Production of Bone Regeneration Material Kit and Paste-Like Bone Regeneration Material A bone regeneration material kit was composed of the resulting powder mixture of the inositol hexaphosphate-adsorbing hydroxyapatite particles and the ground product of α-tricalcium phosphate particles, the resulting thermally crosslinked gelatin particles, and an aqueous medium (10% chitosan, 2.5% sodium dihydrogen phosphate). To the resulting powder mixture was blended the thermally crosslinked gelatin particles in an amount of 10% by weight relative to the amount of the powder mixture. Then, 700 to 800 μL of the aqueous medium was added to a 1.0 g portion of the resulting mixture. They were mixed for 120 seconds to prepare a paste-like bone regeneration material.

Experimental Example 2

A bone regeneration material kit and a paste-like bone regeneration material were produced as in Experimental Example 1, except that the amount of thermally crosslinked gelatin particles was 5% by weight.

Comparative Examples 1 and 2

A bone regeneration material kit and a paste-like bone regeneration material were produced as in Experimental Example 1 or 2, except that hydroxyapatite particles to which no inositol hexaphosphate was adsorbed were used instead of the inositol hexaphosphate-adsorbing hydroxyapatite particles.

The hydroxyapatite particles to which no inositol hexaphosphate was adsorbed were prepared by stirring the wet-synthesized hydroxyapatite powder and purified water with a planetary ball mill.

Reference Example

A bone regeneration material kit was composed of calcium phosphate particles having an average particle size of 10 μm to which no inositol hexaphosphate was adsorbed (75% by weight of α-tricalcium phosphate, 18% by weight of tetracalcium phosphate, 5% by weight of calcium hydrogen phosphate dihydrate, and 2% by weight of hydroxyapatite), thermally crosslinked gelatin particles, and an aqueous medium (aqueous solution containing 5.4% chondroitin sodium sulfate, 13% disodium succinate anhydrous, and 0.3% sodium bisulfite). To the calcium phosphate particles was blended the thermally crosslinked gelatin particles in an amount of 10% by weight relative to the amount of the calcium phosphate particles. Then, 700 μL of the aqueous medium was added to a 1.5 g portion of the resulting mixture. They were mixed for 120 seconds to prepare a paste-like bone regeneration material.

(Evaluation)

The paste-like bone regeneration materials prepared in the experimental examples, the comparative examples, and the reference example were evaluated in the following way. Table 1 shows the results.

The compressive strength of the resulting cured product was measured using a universal tester (EZ-Graph, produced by SHIMADZU CORPORATION) at a test speed of 0.5 mm/min.

The bulk density (g/cm$^3$) was calculated by measuring the diameter, height, and weight of the cured product.

TABLE 1

| | Paste-like bone regeneration material | | | | Evaluation | | | | |
|---|---|---|---|---|---|---|---|---|---|
| | Powder mixture (ratio by weight) | | | | | | | Cured product | |
| | Inositol hexaphosphate-adsorbing hydroxyapatite particles | Hydroxyapatite particles with no adsorption of inositol hexaphosphate | Ground product of α-Tricalcium phosphate particles | Amount of crosslinked gelatin particles (% by weight) | Setting time (min) Initial | Final | Anti-washout property | Compressive strength (MPa) | Bulk density (g/cm$^3$) |
| Experimental Example 1 | 0 | — | 100 | 10 | 5 | 6 | x | 10.5 | 1.3 |
| | 10 | — | 90 | 10 | 6 | 7 | ○ | — | — |
| | 20 | — | 80 | 10 | 6 | 7 | ○ | 12.1 | 1.3 |
| | 50 | — | 50 | 10 | 12 | 25 | ○ | 8.6 | 1.3 |
| | 80 | — | 20 | 10 | 22 | 40 or more | Δ | 3.7 | 1.2 |
| | 100 | — | 0 | 10 | 100 or more | 100 or more | Δ | 2.7 | 1.4 |
| Experimental Example 2 | 20 | — | 80 | 5 | 6 | 7 | ○ | 17.0 | 1.4 |
| Comparative Example 1 | — | 20 | 80 | 10 | 6 | 7 | x | 6.1 | 1.3 |
| Comparative Example 2 | — | 20 | 80 | 5 | 6 | 7 | Δ | 10.0 | 1.4 |
| Reference Example | Calcium phosphate particles | | | 10 | 8 | 100 or more | x | 2.7 | 1.4 |

(1) Evaluation of Setting Time of Paste-Like Bone Regeneration Material

The paste-like bone regeneration material immediately after production was packed in a split mold with a diameter of 6.0 mm and a height of 12 mm, and cured for a specific time in a thermo-hygrostat at 37° C. and a relative humidity of 100%.

The hardness of the product was measured for every curing time in accordance with JIS T 6602. The time required to achieve gillmore (lighter) was defined as the initial setting time, and the time required to achieve gillmore (heavier) was defined as the final setting time.

(2) Evaluation of Anti-Washout Property

The paste-like bone regeneration material immediately after production was packed in a split mold with a diameter of 6.0 mm and a height of 12 mm, and cured at room temperature for five minutes. The resulting cured product immediately after curing was put into distilled water, and allowed to stand at room temperature for 24 hours. Then, the state of the cured product in the distilled water was visually observed, and the anti-washout property was evaluated based on the following criteria.

Good (○): little disintegration was observed
Fair (Δ): slight disintegration was observed at an end area
Bad (x): a product completely disintegrated (3) Evaluation of Compressive Strength and Bulk Density of Cured Product The paste-like bone regeneration material immediately after production was packed in a split mold with a diameter of 6 mm and a height of 12 mm, and aged in a thermo-hygrostat at 37° C. and relative humidity of 100% for 24 hours. Then, a sample was taken out from the split mold. Thus, a cured product was obtained.

INDUSTRIAL APPLICABILITY

The present invention can provide a bone regeneration material kit, a paste-like bone regeneration material, a bone regeneration material, and a bone bonding material, which contain particles comprising a bioabsorbable polymer; and can fill a bone defect or damage and secure the mechanical strength of the bone in the short term and can promote regeneration of the patient's own bone in the long term; and can exhibit anti-washout properties after filling even when they are in contact with water such as blood or biological fluids.

The invention claimed is:

1. A bone regeneration material kit comprising:
   a particle comprising a calcium salt and having an inositol phosphate or salt thereof adsorbed on the surface;
   a particle comprising a calcium phosphate compound and having no inositol phosphate or salt thereof adsorbed on the surface;
   wherein a blend ratio of the particle comprising a calcium salt and having an inositol phosphate or salt thereof adsorbed on the surface and the particle comprising a calcium phosphate compound and having no inositol phosphate or salt thereof adsorbed on the surface is within the range of 10:90 to 50:50 by weight;
   a particle comprising a bioabsorbable polymer; and
   an aqueous medium.

2. The bone regeneration material kit according to claim 1,
   wherein the inositol phosphate or salt thereof is inositol hexaphosphate.

3. The bone regeneration material kit according to claim 1,
wherein the particle comprising a bioabsorbable polymer is a particle comprising crosslinked gelatin.

4. The bone material regeneration kit of claim 1, wherein the calcium salt is a hydroxyapatite.

5. The bone material regeneration kit of claim 1, wherein the calcium phosphate compound comprises α-tricalcium phosphate and β-tricalcium phosphate.

6. A paste-like bone regeneration material comprising the bone regeneration material kit according to claim 1,
the paste-like bone regeneration material being a paste prepared by mixing the particle comprising a calcium salt and having an inositol phosphate or salt thereof adsorbed on the surface; the particle comprising a calcium phosphate compound and having no inositol phosphate or salt thereof adsorbed to the surface, the particle comprising a bioabsorbable polymer; and the aqueous medium.

7. A bone regeneration material prepared by curing the paste-like bone regeneration material according to claim 6.

* * * * *